United States Patent [19]

Redmond et al.

[11] Patent Number: 4,863,088
[45] Date of Patent: Sep. 5, 1989

[54] SURGICAL STAPLING INSTRUMENT

[75] Inventors: Russell J. Redmond, Goleta; Thomas F. Banks, Santa Barbara, both of Calif.; Alan J. Solyntjes, Richfield, Minn.

[73] Assignee: Minnesota Mining and Manufacturing Company, St. Paul, Minn.

[21] Appl. No.: 166,037

[22] Filed: Mar. 9, 1988

[51] Int. Cl.⁴ .................... A61B 17/04; A61B 17/11
[52] U.S. Cl. ........................ 227/19; 227/DIG. 1; 128/334 R
[58] Field of Search ............... 227/19, 144; 128/337, 128/334 R

[56] References Cited

U.S. PATENT DOCUMENTS

| 3,490,675 | 1/1970 | Green et al. | 227/19 |
| 3,499,591 | 3/1970 | Green | 227/76 |
| 3,744,495 | 7/1973 | Johnson | 227/144 X |
| 4,290,542 | 9/1981 | Fedotov et al. | 227/155 |
| 4,429,695 | 2/1984 | Green | 128/305 |
| 4,520,817 | 6/1985 | Green | 128/305 |

FOREIGN PATENT DOCUMENTS 2445132  7/1980  France .

OTHER PUBLICATIONS

Surgical Stapling, Gastric and Small Bowell Procedures, vol. 1, ISBN 0-937433-00-4, Library of Congress Catalog No. 85-082599.

The ILA Stapler, Catalog #3957.

Primary Examiner—Donald R. Schran
Assistant Examiner—James L. Wolfe
Attorney, Agent, or Firm—Donald M. Sell; Walter N. Kirn; Stephen W. Bauer

[57] ABSTRACT

A stapling instrument including two elongate structural members each comprising a handle part with a jaw part projecting from a first end. The structural members have pivot means at second ends of their handle parts adapted for free engagement and disengagement and relative pivotal movement of the structural members between open and closed positions. An elongate locking member is mounted one one of the structural members for pivotal movement to a locking position generally aligned with its handle part where the locking member can be releasably retained to forcefully move the structural members to their closed position so that high compressive forces can be applied to tissues between the jaw parts. Staples from a cartridge along one jaw part can then be driven through the tissue and closed against an anvil along the other jaw part. One of the structural members has a support element in contact with the other of the structural members transverse of a space between the handle parts when the structural members are in their closed position to restrict bending and movement of the handle parts toward each other in response to separating forces applied between the jaw parts as a result of compressed tissues so that the staples can be properly closed.

14 Claims, 3 Drawing Sheets

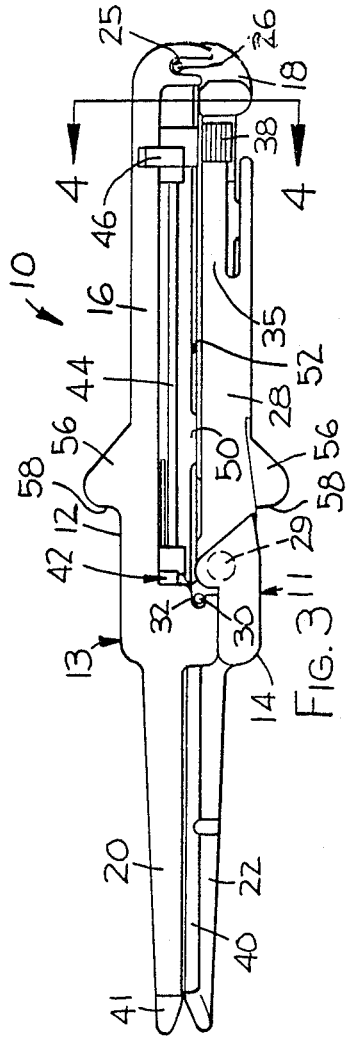
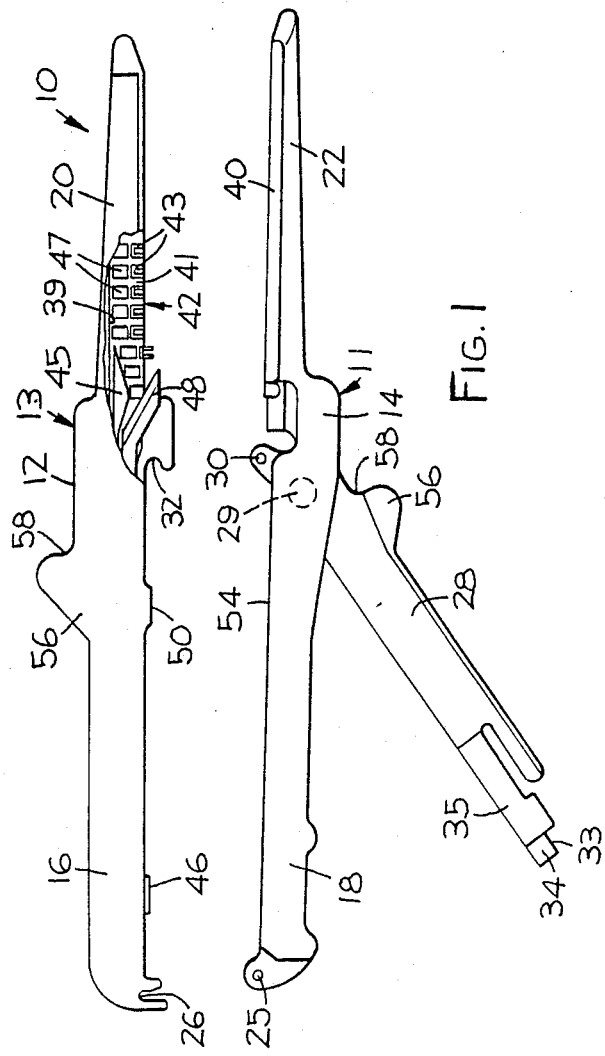
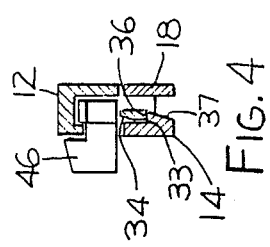

SURGICAL STAPLING INSTRUMENT

TECHNICAL FIELD

The present invention relates to surgical stapling instruments, and particularly to the type of surgical stapling instruments used for applying parallel rows of staples through compressed living tissue.

BACKGROUND ART

Surgical stapling instruments used for applying parallel rows of staples through compressed living tissue are well known in the art, and are commonly used in transecting or reconnecting intestinal, gastric, or lung tissue.

One known surgical stapling instrument of this type has been in use for many years, and is currently available under the trade designation "The ILA Stapler", catalog #3957 by Minnesota Mining and Manufacturing Company, St. Paul, Minn., the use of which stapler is described in a publication entitled "Surgical Stapling, Gastric and Small Bowel Procedures, Volume I", ISBN 0-937433-00-4, Library of Congress Catalog Number 85-082599 available from Minnesota Mining and Manufacturing Company, St. Paul, Minn., the content whereof is incorporated herein by reference. That stapling instrument comprises first and second elongate structural members each comprising a handle part and a jaw part projecting from a first end of the handle part. The structural members have pivot means at second ends of their handle parts adapted for free engagement and disengagement in a plane normal to the directions in which the members are elongate, which pivot means afford, when engaged, relative pivotal movement of the structural members in said plane between a closed position with the jaw parts in closely spaced relationship, and an open position with the jaw parts spaced farther from each other than in the closed position. An elongate locking member having a pivot point closely adjacent a first end is mounted at its pivot point on the first end of the second structural member for pivotal movement around an axis generally normal to said plane between a locking position generally aligned with the handle part of the second structural member, and a release position with a second end of the locking member spaced from the second end of the second structural member. The first end of the locking member and the handle part of the first structural member adjacent its first end have surfaces adapted, when the pivot means are engaged and the structural members are in their open position, for engagement during movement of the locking member from its release position to its locking position to forcefully move the structural members to their closed position so that high compressive forces can be applied on tissues to be stapled between the jaw parts of the structural members, and means adapted for releasable engagement between the elongate locking member and the second structural member are provided for releasably holding the locking member in its locking position and thus maintain any compressive forces applied between the jaw parts. The stapling instrument is adapted to have a removable anvil positioned along one of the jaw parts, and a cartridge containing a plurality of staples disposed in rows positioned along the other of the jaw parts in opposition to the anvil, and the cartridge includes manually actuatable means for sequentially ejecting the staples from the cartridge to press the staples against the anvil to engage and close the staples in tissues between the jaw parts when the structural members are in their closed position. Additionally, if desired, the cartridge can include a knife that moves along and bridges between the cartridge and anvil to cut tissues between the rows of applied staples.

Typically, the lengths of the rows of staples applied by such prior art stapling instruments have been limited in length to about 50 millimeters (2 inches) because compression of tissues between jaw parts of sufficient length to apply longer rows would cause such jaw parts to deflect excessively away from each other and result in improper spacing between the anvil and cartridge, particularly near the distal ends of the jaw parts, and incomplete closure of the staples resulting in poor hemostasis in the tissues being stapled.

One proposed solution to this problem described in U.S. Pat. No. 4,429,695 has been to provide supports at opposite ends of a knife that cuts between the rows of staples, which supports are moved along the jaw parts with the knife and the means for sequentially ejecting the staples against the anvil to hold the anvil and cartridge in the proper spaced relationship as the staples are ejected and closed. The use of such supports, however, requires jaw parts of sufficiently large cross sectional area to receive them, moving such supports along the jaw parts increases the force needed to operate the stapling instrument, particularly when stapling tissue that is highly compressed so that the supports must remove deflection from between the jaw parts as it moves, and the solution only works where a knife is used to cut tissue between the rows of staples, which cutting is not desired in all uses for such stapling instruments.

DISCLOSURE OF INVENTION

The present invention provides a solution to the problem of excessive deflection of jaw parts away from each other as a result of tissue compressive forces in the type of stapling instrument described above, which solution does not require the movement of supports along the jaw parts, allows the instrument to be used with or without a knife for cutting between applied row of staples, can reduce the deflection between the jaw parts in "The ILA Stapler" stapling instrument described above that delivers 50 millimeter long rows of staples, and allows scale up of that instrument to one that will deliver at least 100 millimeter long rows of staples.

According to the present invention there is provided a stapling instrument of the type described above that comprises first and second elongate structural members each comprising a handle part and a jaw part projecting from a first end of the handle part. The structural members have pivot means at second ends of their handle parts adapted for free engagement and disengagement in a plane normal to the directions in which the structural members are elongate, which pivot means afford, when engaged, relative pivotal movement of the structural members in said plane between a closed position with the jaw parts in closely spaced relationship, and an open position with the jaw parts spaced farther from each other than in the closed position. An elongate locking member having a pivot point closely adjacent a first end is mounted at its pivot point on the first end of the second structural member for pivotal movement around an axis generally normal to said plane between a locking position generally aligned with the handle part of the second structural member, and a release position with the second end of the locking member spaced from the second end of the second structural member. The first end of the locking member and the handle part of the first structural member adjacent its first end have surfaces adapted, when the pivot means are engaged with the structural members in their open position, for engagement during movement of the locking member from its release position to its locking position to forcefully move the structural members to the closed position so that high compressive forces can be applied to tissues between the jaw parts of the structural members, and means adapted for releasable engagement between the elongate locking member and the second structural member are provided for releasably holding the locking member in the locking position to thus maintain any compressive forces applied between the jaw parts. The stapling instrument is adapted to have a removable anvil positioned along one of the jaw parts, and a cartridge containing a plurality of staples disposed in rows positioned along the other of the jaw parts in opposition to the anvil, which cartridge includes manually actuatable means for sequentially ejecting the staples from the cartridge and pressing the staples against the anvil to engage and close the staples in tissues between the jaw parts when the structural members are in the closed position. Also, if desired, that cartridge could include a knife that moves along and cuts tissues between the rows of applied staples.

Applicants have analyzed that stapling instrument by structural analysis, and discovered that the deflection of the jaw parts when they are used to compress tissue results primarily because the handle parts of the structural members in their closed position define a space between the structural members over the majority of the distance between the first and second ends of the handle parts. This space allows the handle parts to bend so that their centers deflect toward each other while the jaw parts effectively pivot around the surfaces of the structural members in engagement with each other at the first ends of the handle parts, resulting in separation between the jaw parts increasing toward their distal ends.

While this primary cause of the deflection problem could be solved by eliminating the space between the handle parts of the structural members when they are in their closed position, the tolerances required to provide such line to line contact would be difficult to achieve, and the movement of the handle parts to their closed position could trap part of a users glove or skin between the portions of the handle parts intended to contact, which, because of the high mechanical advantage applied through the locking member to move the structural members to that closed position, could crush, cut or otherwise damage such a trapped part of a users glove or skin.

Thus, in the stapling instrument according to the present invention one of the structural members has a support element in contact with the other of the structural members transverse of the space between the handle parts when the structural members are in their closed position. Preferably, that support element should be positioned away from the first ends of the handle parts in the range of about one eighth to one half the distance between their first and second ends to restrict bending and movement of the handle parts toward each other in response to separating forces applied between the jaw parts as a result of compressed tissues so that the proper spacing will be maintained between the jaw parts and the staples can be properly closed therebetween. The selected location of the support part within this range is a compromise between a position midway between the ends of the handle parts that would have the maximum effect of reducing deflection between the jaw parts, and a location that minimizes the possibility of trapping part of a users glove or skin between the support part and the structural member it contacts, such as a location about ¼ the distance between their first and second ends measured from their first ends.

Also, the support element can either engage a planar surface disposed at a right angle to said plane on the structural member it contacts, or an end of the support element can be received in a socket formed in the other of the structural members so that it not only restricts deflection of the handle parts toward each other, but also prevents any transverse deflection of the handle parts and corresponding transverse or scissors-like deflections of the jaw parts relative to each other.

BRIEF DESCRIPTION OF DRAWINGS

The present will be further described with reference to the drawing wherein like reference numerals to like parts in the several views, and wherein:

FIG. 1 is a first side view of a surgical stapling instrument according to the present invention showing two assemblies of the instrument separated from each other and having parts broken away to show details;

FIG. 3 is a second side view of the surgical stapling instrument of FIG. 1 showing the two assemblies of the instrument each other in a closed position;

FIG. 4 is a sectional view taken approximately along line 4—4 of FIG. 3;

DETAILED DESCRIPTION

Figure 2:
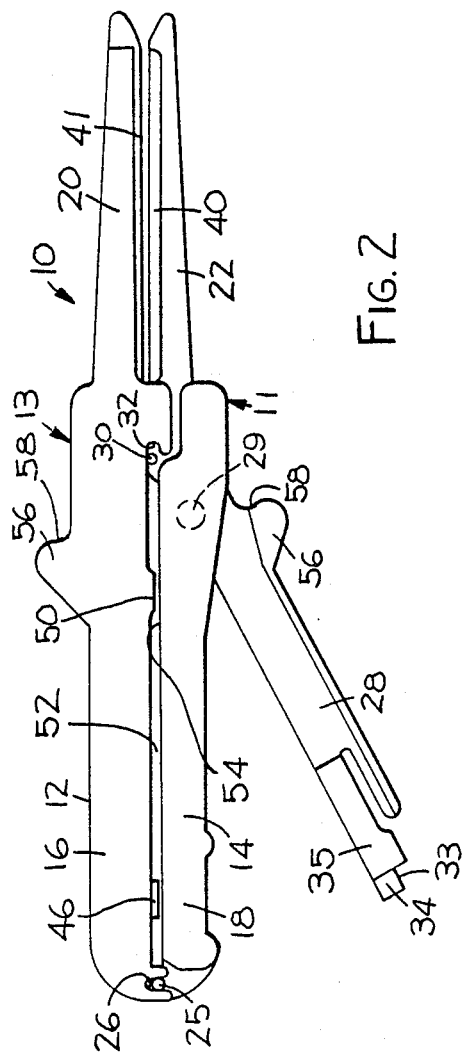
FIG 2 is a side view of the surgical stapling instrument of FIG. 1 showing the two assemblies of the instrument with each other in an open position.

Referring now to FIGS. 1 through 5 of the drawing, there is shown a first embodiment of a surgical stapling instrument 10 according to the present invention, generally designated by the reference numeral 10 and comprising two separable assemblies 11 and 13.

Generally the surgical stapling instrument 10 comprises first and second elongate structural members 12 and 14 each comprising a handle part 16 and 18 respectively, and a jaw part 20 and 22 respectively projecting from a first end of the handle part 16 or 18. The structural members 12 and 14 have pivot means at second ends of their handle parts 16 and 18 comprising two opposite axially parallel outwardly projecting pins 25 on the second structural member 14 and generally U-shaped journal surfaces 26 on the first structural member 12 adapted and positioned for free engagement and disengagement in a plane normal to the directions in which the structural members 12 and 14 are elongate, which pivot means affords, when engaged, relative pivotal movement of the structural members 12 and 14 in said plane between a closed position (FIGS. 3 and 5) with the jaw parts 20 and 22 in closely spaced relationship, and an open position (FIG. 2) with the jaw parts 20 and 22 spaced farther from each other than in the closed position. An elongate locking member 28 having a pivot point at a pin 29 closely adjacent a first end of the locking member 28 is mounted by the pin 29 on the first end of the second structural member 14 for pivotal movement around an axis generally normal to said plane between a locking position (FIGS. 3 and 5) generally aligned with the handle part 18 of the second structural member 14, and a release position (FIGS. 1 and 2) with the second end of the locking member 28 spaced from the second end of the second structural member 14. The first end of the locking member 28 and the handle part 16 of the structural member 12 adjacent its first end have surfaces provided by two opposite axially parallel outwardly projecting pins 30 on the locking member 28 and side surfaces of generally U-shaped surfaces 32 on the first structural member 12 opening toward the second end of the first structural member 12 adapted, when the pivot means are engaged with the structural members 12 and 14 in the open position, for engagement during movement of the locking member 28 from its release position (FIG. 2) to its locking position (FIGS. 3 and 5) to forcefully move the structural members 12 and 14 to their closed position so that high compressive forces can be applied to tissues between the jaw parts 20 and 22 of the structural members 12 and 14. Means adapted for releasable engagement between the elongate locking member 28 and the second structural member 14 are provided (FIG. 4) in the form of an edge abutment surface 33 at one end of a cam 34 on a cantilevered transversely flexible part 35 of the locking member 28 in engagement with an edge abutment surface 36 at one end of a cam 37 on the second structural member 14 for releasably holding the locking member 28 in its locking position and thus maintain any compressive forces applied between the jaw parts 20 and 22. The cams 34 and 37 are aligned and oriented to deflect the flexible part 35 and allow the cam 34 to pass around the cam 37 to afford engagement of the edge abutment surfaces 33 and 36 when the locking member 28 is manually pressed to its locking position, and the flexible part 35 can be manually deflected by pressing on the flexible part at a grooved pressure pad 38 to afford separation of the abutment surfaces 33 and 36 and movement of the locking member 28 from its locking to its release position.

The second structural member 14 is adapted to have an elongate removable anvil 40 positioned over and along the jaw part 22 to form the first assembly 11, and the jaw part 20 of the first structural member has an elongate groove 39 (FIG. 1) adapted to receive a cartridge body 41 of a cartridge assembly 42 to form the second assembly 13. The cartridge body 41 contains a plurality of staples 43 disposed in rows oriented longitudinally of the jaw part 20 in opposition to the anvil 40 when the structural members 12 and 14 are in their closed position. Also, the cartridge assembly 42 includes manually actuatable means including cam like drivers 45 fixed at one end of a drive rod 44 and adapted to be moved through longitudinal slots in the cartridge body 41 by manually pressing on an actuating tab 46 fixed at the end of the drive rod 44 opposite the drivers 45 for sequentially ejecting the staples from the cartridge body 41 by camming plungers 47 under the staples 43 toward a surface of the cartridge body 41 opposite the anvil 40 to thereby press the ejected staples 43 against specially shaped surfaces on the anvil 40 to engage and close the staples 43 in tissues between the jaw parts 20 and 22 when the structural members 12 and 14 are in their closed position. The cartridge assembly 42 can also optionally, as illustrated, include a knife 48 that is also fixed on the end of the drive rod 44 adjacent the drivers 45 so that manual movement of the drivers 45 to eject and close the staples 43 also moves the knife 48 along the jaw parts 20 and 22 with the distal end of the knife 48 in a slot in the anvil 40 to cut tissues between the rows of applied staples.

Figure 5:
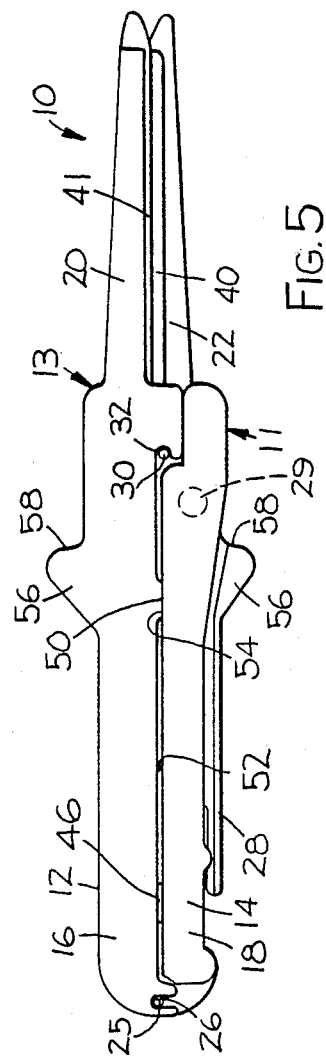
FIG. 5 is a first side view of the surgical stapling instrument of 1 showing the two assemblies of the instrument with each other in the closed position.

The structure of the stapling instrument 10 as described above in this Detailed Description portion of this specification is essentially the same as that of the surgical stapling instrument sold under the trade designation "The ILA Stapler" by Minnesota Mining and Manufacturing Company, St. Paul, Minn. The novel structure of the stapling instrument 10 that distinguishes the present invention from "The ILA Stapler" stapling instrument and which allows the stapling instrument 10 to be made in a size that can deliver a 100 millimeter long row of staples is that one of the structural members 12 or 14 (as illustrated, the first structural member 12) has a support element 50 about ½ inch long in the direction in which the structural member 12 is elongate, which support element 50 is in contact with the other of the structural members 12 or 14 (as illustrated, the second structural member 14) transverse of a space 52 defined between the handle parts 16 and 18 of the structural members 12 and 14 when those structural members 12 and 14 are in their closed position (FIGS. 3 and 5). When the structural members 12 and 14 are in their closed position, the support element 50 contacts a planar surface 54 on the second structural member 14 disposed at a right angle to the plane in which the structural members 12 and 14 pivot relative to each other about the pins 25 at a position spaced about one quarter the distance between the first and second ends of the handle parts 16 and 18 to restrict bending and deflection of the handle parts 16 and 18 toward each other in response to separating forces applied to the jaw parts 20 and 22 by tissues compressed between the jaw parts 20 and 22. As illustrated, the support element 50 is positioned between opposite manually engageable projections 56 on the first structural member 12 and locking member 28 that have engagement surfaces 58 disposed at right angles to the length of the structural members 12 and 14 adjacent the first end of the handle parts 16 and 18 when the locking member 28 is in its locking position. The engagement surfaces 58 can be engaged with the fingers of a user's hand while the thumb of that hand is used to press the actuating tab 46 toward the jaw parts 20 and 22 to thereby apply the staples to tissues between the jaw parts 20 and 22. To move the structural members 12 and 14 to their closed position, a user has a tendency to grasp the handle parts 16 and 18 and locking member 28 between their second ends and the adjacent sides of the projections 56 so that the location of the support element 50 between the projections 56 limits the possibility that a part of a user's glove or skin will become entrapped between the support element 50 and the second structural member 14.

Figure 7:
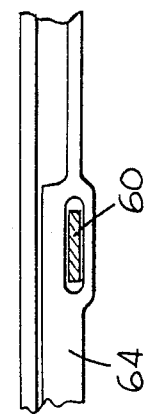
FIG. 7 is a fragmentary sectional view taken approximately along line 7—7 of FIG. 6.
Figure 6:
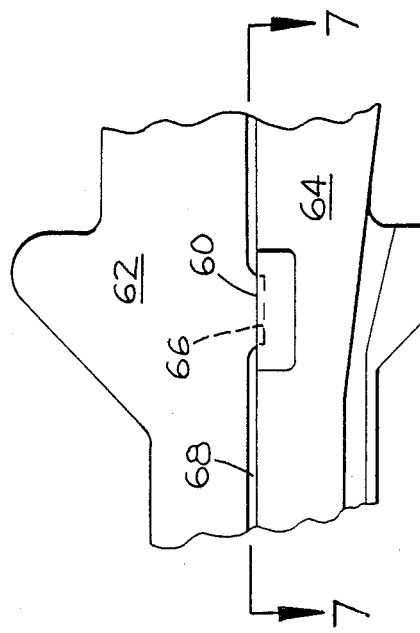
FIG. 6 is an enlarged fragmentary side view of an alternative of the surgical stapling instrument according to the present invention.

Referring now to FIGS. 6 and 7 there is shown an optional structure for a support element 60 on a structural member 62 that can otherwise have the same structure as the first structural member 12, and for the portion of a structural member 64 the support element 60 engages, which structural member 64 may otherwise have the same structure as the second structural member 14. The structural member 64 contacted by the support element 60 has surfaces defining a socket 66, and a distal end portion of the support element 60 engages the surfaces defining the socket 66 when the structural members 62 and 64 are in their closed position. Such engagement of the support element 60 with the surfaces defining the socket 66 not only restricts deflection of the handle parts of the structural members 62 and 64 toward each other along a space 68 therebetween, but also prevents any transverse deflection of those handle parts in a direction at right angles to the plane in which the structural members 62 and 64 pivot and thereby limits corresponding transverse or scissors-like deflections of jaw parts of the structural members 62 and 64 relative to each other.

The present invention has now been described with reference to two embodiments thereof. It will be apparent to those skilled in the art that many changes can be made in the embodiments described without departing from the scope of the present invention, including the location of the support element between the first and second ends of the handle parts of surgical stapling instrument. Thus the scope of the present invention should not be limited to the structures descried in this application, but only by structures described by the language of the claims and the equivalents of those structures.

We claim:

1. A surgical stapling instrument comprising:

first and second structural members each being elongate in a first direction and each comprising a handle part having first and second ends and a jaw part projecting from said first end, said structural members having pivot means at said second ends adapted for free engagement and disengagement in a plane normal to said first directions for affording, when engaged, relative pivotal movement of said structural members in said plane between a closed position with said jaw parts in closely spaced relationship, and an open position with said jaw parts spaced farther from each other than in said closed position, said handle parts of said structural members in said closed position defining a space between said handle parts over the majority of the distance between said first and second ends when said structural members are in said closed position;

an elongate locking member having first and second ends and a pivot point closely adjacent the first end of the locking member, the pivot point of said locking member being mounted on said second structural member adjacent the first end of said second structural member for pivotal movement around an axis generally normal to said plane between a locking position generally aligned with the handle part of said second structural member, and a release position with the second end of said locking member spaced from the second end of said second structural member, said first end of said locking member and said handle part of said first structural member adjacent the first end of said first structural member having surfaces adapted, when said pivot means are engaged with said structural members in said open position, for engagement during movement of said locking member from said release position to said locking position to forcefully move said structural members to said closed position; and means adapted for releasable engagement between said elongate locking member and said second structural member for holding said locking member in said locking position;

said stapling instrument having an anvil surface along one of said jaw parts, a cartridge including a plurality of staples along the other of said jaw parts, and manually actuatable means for sequentially pressing said staples within said cartridge against said anvil to engage and close the staples in tissues between said jaw parts when said structural members are in said closed position; and one of said structural members having a support element in contact with the other of said structural members transverse of said space when said structural members are in said closed position, said support element being spaced between said ends of said handle parts to restrict bending and deflection of said handle parts toward each other in response to separating forces applied to said jaw parts by tissues compressed between said jaw parts.

2. A surgical stapling instrument according to claim 1 wherein when said structural members are in said closed position, said support element contacts a planar surface disposed at a right angle to said plane on the structural member contacted by said structural element.

3. A surgical sapling instrument according to claim 1 wherein said support element is spaced away from said first ends of said handle parts in the range of about one eighth to one half the distance between said first and second ends of said handle parts 4. A surgical stapling instrument according to claim 1 wherein said support element has a length of about $\frac{1}{2}$ inch in said first direction.

5. A surgical stapling instrument according to claim 4 wherein said support element is spaced away from said first ends of said handle parts about one quarter the distance between said first and second ends of said handle parts.

6. A surgical stapling instrument according to claim 1 further including manually engageable projections along said handle parts having engagement surfaces disposed at right angles to said first direction and facing said jaw parts, said engagement surfaces being adapted to be engaged with the fingers of a users hand while the thumb of that hand is used to operate said manually actuatable means, and said support element is positioned between said manually engageable projections.

7. A surgical stapling instrument comprising:

first and second structural members each being elongate in a first direction and each comprising a handle part having first and second ends and a jaw part projecting from said first end, said structural members having pivot means at said second ends adapted for free engagement and disengagement in a plane normal to said first directions for affording, when engaged, relative pivotal movement of said structural members in said plane between a closed position with said jaw parts in closely spaced relationship, and an open position with said jaw parts spaced farther from each other than in said closed position, said handle parts of said structural members in said closed position defining a space between said handle parts over the majority of the distance between said first and second ends when said structural members are in said closed position;

an elongate locking member having first and second ends and a pivot point closely adjacent the first end of the locking member, the pivot point of said locking member being mounted on said second structural member adjacent the first end of said second structural member for pivotal movement around an axis generally normal to said plane between a locking position generally aligned with the handle part of said second structural member, and a release position with the second end of said locking member spaced from the second end of said second structural member, said first end of said locking member and said handle part of said first structural member adjacent the first end of said first structural member having surfaces adapted, when said pivot means are engaged with said structural members in said open position, for engagement during movement of said locking member from said release position to said locking position to forcefully move said structural members to said closed position; and means adapted for releasable engagement between said elongate locking member and said second structural member for holding said locking member in said locking position;

said stapling instrument having an anvil surface along one of said jaw parts, a cartridge including a plurality of staples along the other of said jaw parts, and manually actuatable means for sequentially pressing said staples within said cartridge against said anvil to engage and close the staple in tissues between said jaw parts when said structural members are in said closed position; and one of said structural members having a support element in contact with the other of said structural members transverse of said space when said structural members are in said closed position, said support element being spaced between said ends of said handle parts to restrict bending and deflection of said handle parts toward each other in response to separating forces applied to said jaw parts by tissues compressed between said jaw parts;

said structural members contacted by said support element having surface defining a socket, and a distal end portion of said support element is engages said surfaces defining said socket when said structural elements are in said closed position.

8. A surgical stapling instrument comprising:

first and second structural members each being elongate in a first direction and each comprising a handle part having first and second ends and a jaw part projecting from said first end, said structural members having pivot means at said second ends adapted for free engagement and disengagement in a plane normal to said first directions for affording, when engaged, relative pivotal movement of said structural members in said plane between a closed position with said jaw parts in closely spaced relationship, and an open position with said jaw parts spaced farther from each other than in said closed position, said handle parts of said structural members in said closed position defining a space between said handle parts over the majority of the distance between said first and second ends when said structural members are in said closed position;

an elongate locking member having first and second ends and a pivot point closely adjacent the first end of the locking member, the pivot point of said locking member being mounted on said second structural member adjacent the first end of said second structural member for pivotal movement around an axis generally normal to said plane between a locking position generally aligned with the handle part of said second structural member, and a release position with the second end of said locking member spaced from the second end of said second structural member, said first end of said locking member and said handle part of said first structural member adjacent the first end of said first structural member having surfaces adapted, when said pivot means are engaged with said structural members in said open position, for engagement during movement of said locking member from said release position to said locking position to forcefully move said structural members to said closed position; and means adapted for releasable engagement between said elongate locking member and said second structural member for releasably holding said locking member in said locking position;

said stapling instrument being adapted to have a removable anvil positioned along one of said jaw parts, and a cartridge assembly including a cartridge containing a plurality of staples disposed in rows positioned along the other of the jaw parts in opposition to the anvil, which cartridge assembly further includes manually actuatable means for sequentially ejecting the staples from the cartridge to press the staples against the anvil and engage and close the staples in tissues between said jaw parts when said structural members are in said closed position; and one of said structural members having a support element in contact with the other of said structural members transverse of said space when said structural members are in said closed position, said support element being spaced between said ends of said handle parts to restrict bending and deflection of said handle parts toward each other in response to separating forces applied to said jaw parts by tissues compressed between said jaw parts.

9. A surgical stapling instrument according to claim 8 wherein when said structural members are in said closed position, said support element contacts a planar surface disposed at a right angle to said plane on the structural member contacted by said structural element.

10. A surgical stapling instrument according to claim 8 wherein said support element is spaced away from said first ends of said handle parts in the range of about one eighth to one half the distance between said first and second ends of said handle parts.

11. A surgical stapling instrument according to claim 8 wherein said support element has a length of about ½ inch in said first direction.

12. A surgical stapling instrument according to claim 11 wherein said support element is spaced away from said first ends of said handle parts about one quarter the distance between said first and second ends of said handle parts.

13. A surgical stapling instrument according to claim 8 further including manually engageable projections along said handle parts having surfaces disposed at right angles to said first direction and facing said jaw parts adapted to be engaged with the fingers of a users hand while the thumb of that hand is used to operate said manually actuatable means, and said support element is positioned between said manually engageable projections.

14. A surgical stapling instrument comprising:

first and second structural members each being elongate in a first direction and each comprising a handle part having first and second ends and a jaw part projecting from said first end, said structural members having pivot means at said second ends adapted for free engagement and disengagement in a plane normal to said first directions for affording, when engaged, relative pivotal movement of said structural members in said plane between a closed position with said jaw parts in closely spaced relationship, and an open position with said jaw parts spaced farther from each other than in said closed position, said handle parts of said structural members in said closed position defining a space between said handle parts over the majority of the distance between said first and second ends when said structural members are in said closed position;

an elongate locking member having first and second ends and a pivot point closely adjacent the first end of the locking member, the pivot point of said locking member being mounted on said second structural member adjacent the first end of said second structural member for pivotal movement around an axis generally normal to said plane between a locking position generally aligned with the handle part of said second structural member, and a release position with the second end of said locking member spaced from the second end of said second structural member, said first end of said locking member and said handle part of said first structural member adjacent the first end of said first structural member having surfaces adapted, when said pivot means are engaged with said structural members in said open position, for engagement during movement of said locking member from said release position to said locking position to forcefully move said structural members to said closed position; and means adapted for releasable engagement between said elongate locking member and said second structural member for releasably holding said locking member in said locking position;

said stapling instrument being adapted to have a removable anvil positioned along one of said jaw parts, and a cartridge assembly including a cartridge containing a plurality of staples disposed in rows positioned along the other of the jaw parts in opposition to the anvil, which cartridge assembly further includes manually actuatable means for sequentially ejecting the staples from the cartridge to press the staples against the anvil and engage and close the staples in tissues between said jaw parts when said structural members are in said closed position; and one of said structural members having a support element in contact with the other of said structural members transverse of said space when said structural members are in said closed position, said support element being spaced between said ends of said handle parts to restrict bending and deflection of said handle parts toward each other in response to separating forces applied to said jaw parts by tissues compressed between said jaw parts;

said structural member contacted by said support element having surfaces defining a socket, and a distal end portion of said support element engages said surfaces defining said socket when said structural elements are in said closed position.

* * * * *

UNITED STATES PATENT AND TRADEMARK OFFICE
CERTIFICATE OF CORRECTION

PATENT NO. : 4,863,088

DATED : September 5, 1989

INVENTOR(S) : Russell J. Redmond, Thomas F. Banks and Alan J. Solyntjes

It is certified that error appears in the above-identified patent and that said Letters Patent is hereby corrected as shown below:

Col. 4, line 22, after "the" insert --accompanying--.

Col. 4, line 28, after "a" insert --first--.

Col. 4, line 33, after "instrument" insert --engaged with--.

Col. 4, line 37, after "of" first occurrence, insert --Figure--.

Col. 4, line 38, after "instrument" insert --engaged--.

Signed and Sealed this

Fifteenth Day of January, 1991

Attest:

HARRY F. MANBECK, JR.

*Attesting Officer*     *Commissioner of Patents and Trademarks*